United States Patent [19]
Cerwin et al.

[11] Patent Number: 6,015,042
[45] Date of Patent: *Jan. 18, 2000

[54] DOUBLE-ARMED SUTURE PACKAGE HAVING RAMPED NEEDLE PARK

[75] Inventors: Robert James Cerwin, Pipersville, Pa.; Deborah M. Transue, Bridgewater; Marvin Alpern, Glen Ridge, both of N.J.

[73] Assignee: Ethicon, Inc., Somerville, N.J.

[*] Notice: This patent is subject to a terminal disclaimer.

[21] Appl. No.: 09/193,188

[22] Filed: Nov. 17, 1998

Related U.S. Application Data

[63] Continuation-in-part of application No. 09/022,581, Feb. 12, 1998, abandoned.

[51] Int. Cl.[7] .................................................. A61B 17/06
[52] U.S. Cl. .......................................... 206/63.3; 206/382
[58] Field of Search ................................. 206/63.3, 227, 206/380, 382, 388, 495

[56] References Cited

U.S. PATENT DOCUMENTS

| | | | |
|---|---|---|---|
| 5,024,322 | 6/1991 | Holzwarth | 206/63.3 |
| 5,279,411 | 1/1994 | Brunken | 206/63.3 |
| 5,344,005 | 9/1994 | Kettner et al. | 206/63.3 |
| 5,601,185 | 2/1997 | Behring et al. | 206/380 |
| 5,732,816 | 3/1998 | Cerwin et al. | 206/63.3 |

Primary Examiner—David T. Fidei
Attorney, Agent, or Firm—Emmil Richard Skula

[57] ABSTRACT

A folder package for surgical sutures. The package has a base panel, a foldably connected cover panel, a foldably connected closure panel, a foldably connected end panel, and a ramp structure. The package also has at least one ramp structure mounted to the base panel. The ramp structure allows sutures to pass over the park without getting hung-up on or in the park.

7 Claims, 14 Drawing Sheets

DOUBLE-ARMED SUTURE PACKAGE HAVING RAMPED NEEDLE PARK

This is a Continuation-In-Part of commonly-assigned U.S. patent application Ser. No. 09/022,581 filed on Feb. 12, 1998, now abandoned.

TECHNICAL FIELD

The field of art to which this invention relates is packaging, in particular, packages for surgical needles and sutures.

BACKGROUND OF THE INVENTION

Folder packages for surgical sutures and surgical needles are well known in the art. Surgical sutures are typically referred to in this art as single-armed or double-armed. Single-armed surgical sutures have a single surgical needle mounted to one end of the suture. In contrast, double-armed needles have a surgical needle mounted to each end of the suture. In a typical double-armed suture folder package, the suture is typically folded in half to form a loop at the suture mid-point such that both ends of the suture and the attached surgical needles are adjacent to each other. Then the loop end of the suture is mounted in a retention means, and both surgical needles (mounted to the ends of the suture) are mounted into a needle park. Alternatively, the ends of the suture adjacent to the needles may be mounted in the needle parks. Typically, multiple double-armed needles are packaged in a folder package.

There is a constant need in this art for improved packages for double-armed and single-armed surgical sutures that are readily removed from a package without any binding or hang-ups.

DISCLOSURE OF THE INVENTION

Therefore, it is an object of the present invention to provide an improved folder package for double-armed suture needles.

It is a further object of the present invention to provide an improved needle park having an adjacent ramped member, which will assist, in preventing double-armed sutures from hanging up in a needle park when the sutures are removed from the package.

It is still yet a further object of the present invention to provide an improved ramped member, which incorporates a needle park.

Accordingly, a folder package for double-armed sutures is disclosed. The package has a base panel, said base panel having opposed first and second major sides and opposed first and second minor sides. A cover panel having opposed first and second major sides and opposed first and second minor sides, is foldably connected along the first minor side of the cover panel to the second major side of the base panel. A closure panel comprising first and second opposed major sides and first and second opposed minor sides is foldably connected along a first major side to the second major side of the cover panel. At least one suture park for retaining a suture is mounted to the base panel. An end panel is foldably connected to the first minor side of the closure panel. There are tab pockets in the closure panel for locking the closure panel to the base panel and cover panel. A tab member extending from the end panel locks the end panel to the cover panel when it is inserted into a tab pocket in the cover panel. A ramp member is mounted to the first minor end of the base panel adjacent to the suture park. The ramp member consists of a connecting panel foldably attached to the top of the base panel and a ramp panel foldably attached to the connecting panel. A plurality of holes is contained in the ramp panel and connecting panel. The ramp panel is locked to the base panel via a tab member extending from the end of the ramp panel. The tab member is inserted into a tab pocket in the base panel.

Yet another aspect of the present invention is a folder package for double-armed sutures having a molded ramp suture park. The package has a base panel, said base panel having opposed first and second major sides and opposed top and bottom minor sides. The base panel has a top and a bottom. A cover panel having opposed first and second major sides and opposed first and second minor sides, is foldably connected along the first minor side of the cover panel to the second major side of the base panel. A closure panel comprising first and second opposed major sides and first and second opposed minor sides is foldably connected along a first major side to the second major side of the cover panel. At least one suture park for retaining a suture is mounted to the base panel. An end panel is foldably connected to the first minor side of the closure panel. There are tab pockets in the closure panel for locking the closure panel to the base panel and cover panel. A tab member extending from the end panel locks the end panel to the cover panel when it is inserted into a tab pocket in the cover panel. A molded suture retaining ramp member is mounted to the base panel adjacent to the top minor side. The ramp member has a base member having a top side and a bottom side. A plurality of projections extends up from the top side of the base member. The projections having a top side, a proximal side, a distal side and opposed end sides. The projections are separated from each other by slots. A plurality of ramped members extends up from the top side of the base member. The ramped members have a sloped top side, a pair of opposed sides, a distal end and a proximal end, wherein the distal side of each ramped member intersects the proximal side of a projection. The proximal end of each ramped member intersects the top side of a base member, and the distal end of the sloped top side intersects the top side of a projection.

These and other features and advantages of the invention will become more apparent from the following description and accompanying drawings.

BEST MODE FOR CARRYING OUT THE INVENTION

Figure 1:
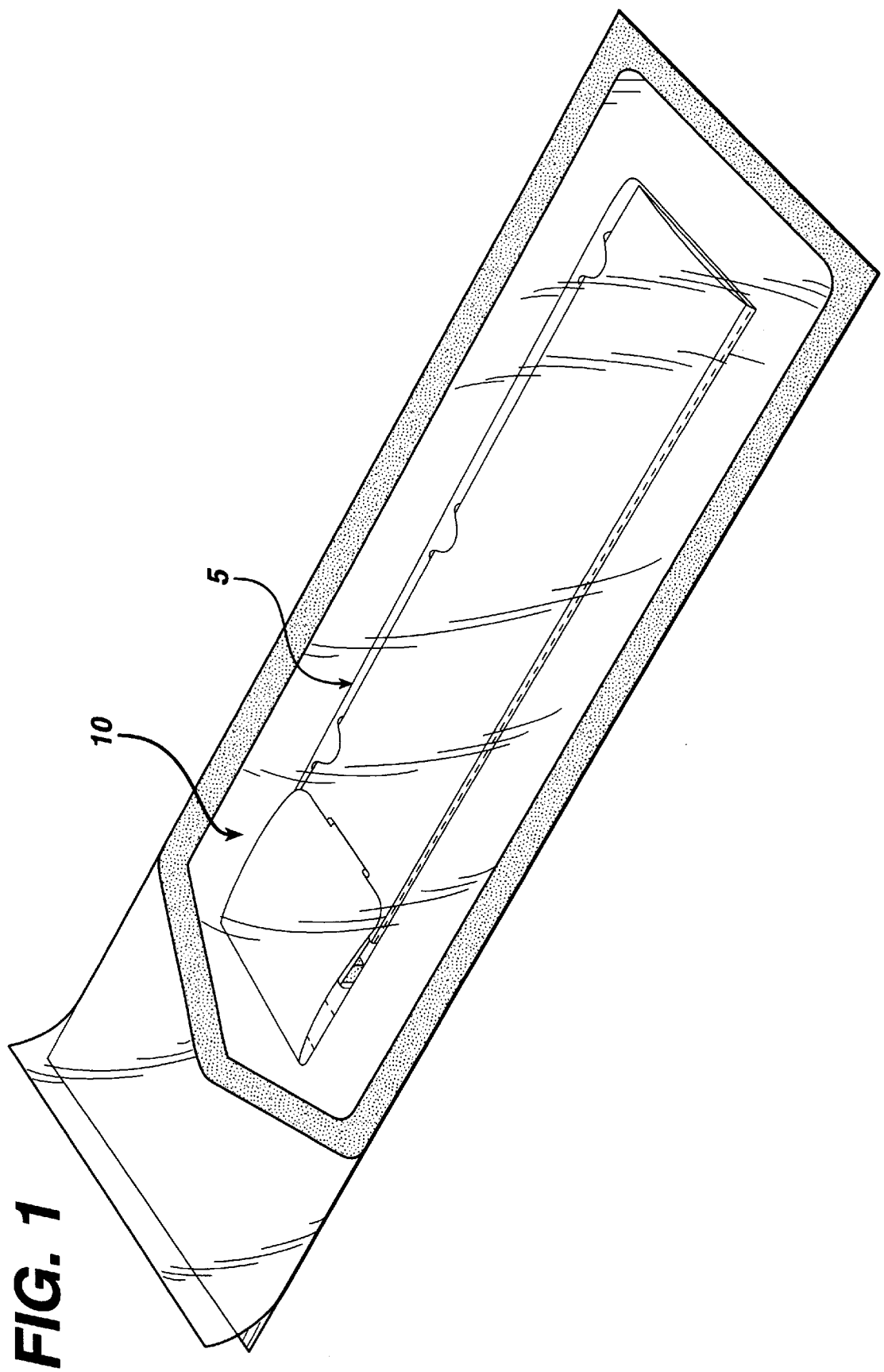
FIG. 1 is a perspective view of a suture package of the present invention contained in an outer sealed pouch.
Figure 2:
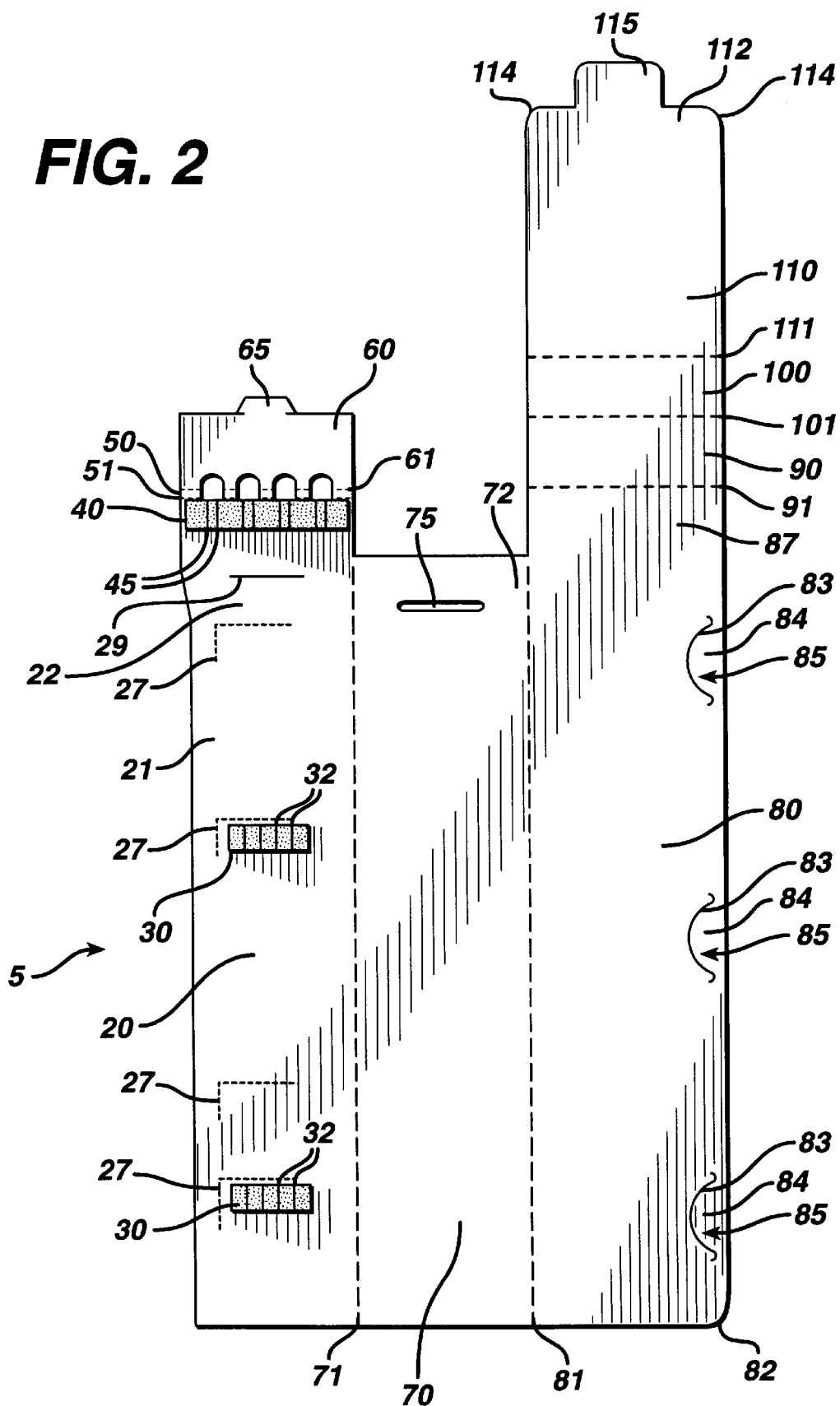
FIG. 2 is a plan view of a suture package of the present invention prior to loading double-armed sutures and prior to folding and assembling.

A perspective view of the package 5 of the present invention is seen in FIG. 1. Package 5 is seen to be fully assembled and contained within a sealed outer blister pack 10. Outer blister pack 10 is a conventional pouch which is preferably permeable to a sterilization gas such as ethylene oxide, although conventional pouches which are impermeable to gases and moisture may be also used. Referring now to FIG. 2, a top view of the foldable package 5 of the present invention is seen prior to folding and assembly. The package 5 is seen to consist of a plurality of foldably connected panels, each panel having a front side and a back side. The package is seen to have a base panel 20, a ramp panel 60, a cover panel 70, a closure panel 80, and an end panel 110. Base panel 20 is seen to be a substantially rectangularly shaped panel having a pair of substantially opposed major sides and a pair of substantially opposed minor sides. The side 21 of base panel 20 is seen to have angulated section 22 such that the top section 23 of base panel 20 is slightly wider than the rest of the panel 20. Foldably attached to the top 24 of base panel 20 along fold line 51 is the connecting panel 50. Connecting panel 50 is seen to be a substantially rectangularly shaped panel. Foldably connected to connecting panel 50 along fold line 61 is the ramp panel 60. Ramp panel 60 is seen to be a substantially rectangularly shaped panel having a pair of substantially opposed major sides and a pair of substantially opposed minor sides. Extending from the top 62 of ramp panel 60 is the tab member 65. The semi-circular openings 55 having opposed straight sides 56 and curved top section 57 are seen to extend through connecting panel 50 into ramp panel 60. Ramp panel 60 and connecting panel 50 form ramp structure 170. Adjacent to fold line 51 is mounted the suture/needle park member 40. Suture/needle park 40 is a conventional foamed polymeric needle park having slits 45 therein to receive and contain either surgical sutures or surgical needles or sections of the surgical needles and the sections of the surgical sutures. Preferably, each slit 45 will contain a single suture section or single needle. The score lines 27 are seen to be contained in base panel 20 at several locations. The score lines 27 are optional and may be used as markers to locate suture parks 30. Shown in FIG. 2 are two suture parks 30 which are conventional foamed polymeric members having slits 32 therein to receive and contain sections of a surgical suture. The number of suture parks 30 used in the packages 5 of the present invention will depend upon the length and type of suture, and various conventional packaging parameters including as type of shipment and storage, type of sterilization, whether the packaging process is manual or automated, etc. The base panel 20 is foldably connected to the cover panel 70 along fold line 71. Cover panel 70 is seen to be a substantially rectangular panel having a pair of substantially opposed major sides and a pair of substantially opposed minor sides. Located toward the top 72 of panel 70 is the tab slot 75. Foldably attached to cover panel 70 along fold line 81 is the closure panel 80. Closure panel 80 is seen to be a substantially rectangular panel having substantially opposed major sides and substantially opposed minor sides. Closure panel 80 is seen to have lower rounded corner 82 and three tab pockets 85 formed by slits 83 and tabs 84. Foldably attached to the top 87 of panel 80 along fold line 91 is the first connecting panel 90. First connecting panel 90 is a substantially rectangular panel having a pair of substantially opposed major sides and a pair of substantially opposed minor sides. Connected to the first connecting panel 90 is the second connecting panel 100. Second connecting panel 100 is connected to first connecting panel 90 along fold line 101. Although it is preferred to have at least one connecting panel between closure panel 80 and end panel 100, the connecting panels may be eliminated if so desired. Foldably connected to the second connecting panel 100 along fold line 111 is the end panel 110. End panel 110 is seen to be substantially rectangularly shaped with a pair of substantially opposed major sides and a pair of substantially opposed minor sides. Extending from the top 112 of the panel 110 is the tab member 115. Panel 110 is seen to have rounded corners 114.

It will be appreciated that both park 40 and one or more parks 30 may have a ramp structure 170 adjacent thereto, although this is not shown in the drawings.

With regard to needle/suture parks 30 and 40, the foam members 30 and 40 may be affixed to the base panel 20 by conventional methods typical in this art. For example, the foam parks may be glued, or mechanically attached. It is particularly preferred in the practice of the present invention to utilize rectangular foam strips having an adhesive pre-applied on one side for the parks 30 and 40. The foam strips are then cut into foam members 30 and 40 having the desired sizes using conventional cutting equipment and processes. Similarly, slits for retaining sutures and/or needles are cut into the non-adhesive side of the foam members. Then, the adhesive side is affixed to the desired location on the base panel. The foam members 30 and 40 will be of sufficient size and shape to effectively retain and protect a suture or surgical needle. If one were willing to accept any disadvantages which may be attendant, if any, foam members 30 and 40 may be replaced by paper members or other conventional needle\suture park members including thermoformed parks, injection molded parks and the like and combinations thereof.

It will also be appreciated by those skilled in the art that various shapes can be effectively used for the parks 30 and 40 including squares, circles, etc. It will also be appreciated by those skilled in the art that the locking means used to secure the package 10 may include any conventional means in addition to tabs and tab pockets such as mechanical fasteners, adhesives, etc.

Figure 15:
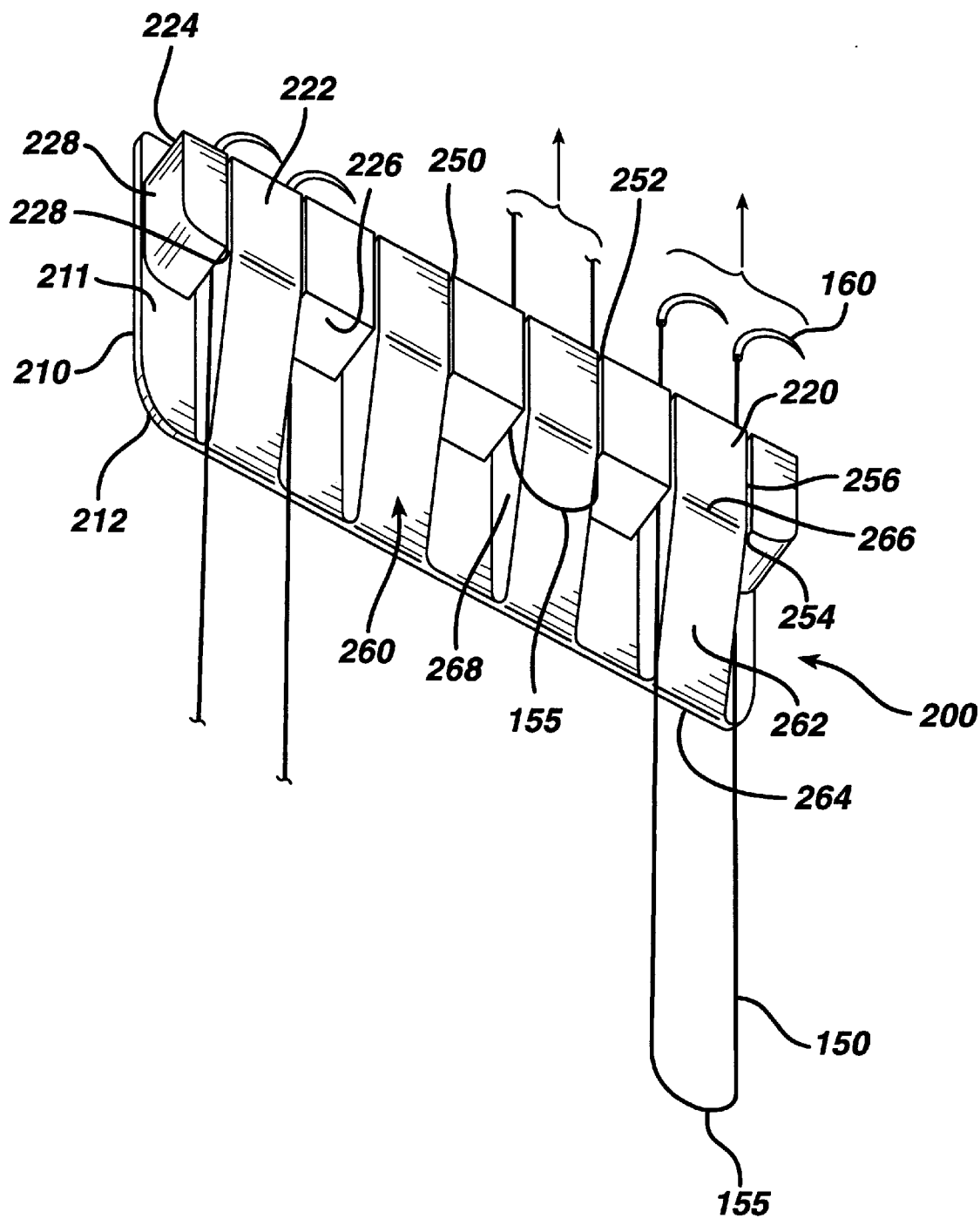
FIG. 15 is a perspective view of a preferred embodiment of a molded ramped needle park useful in the packages of the present invention.
Figure 16:
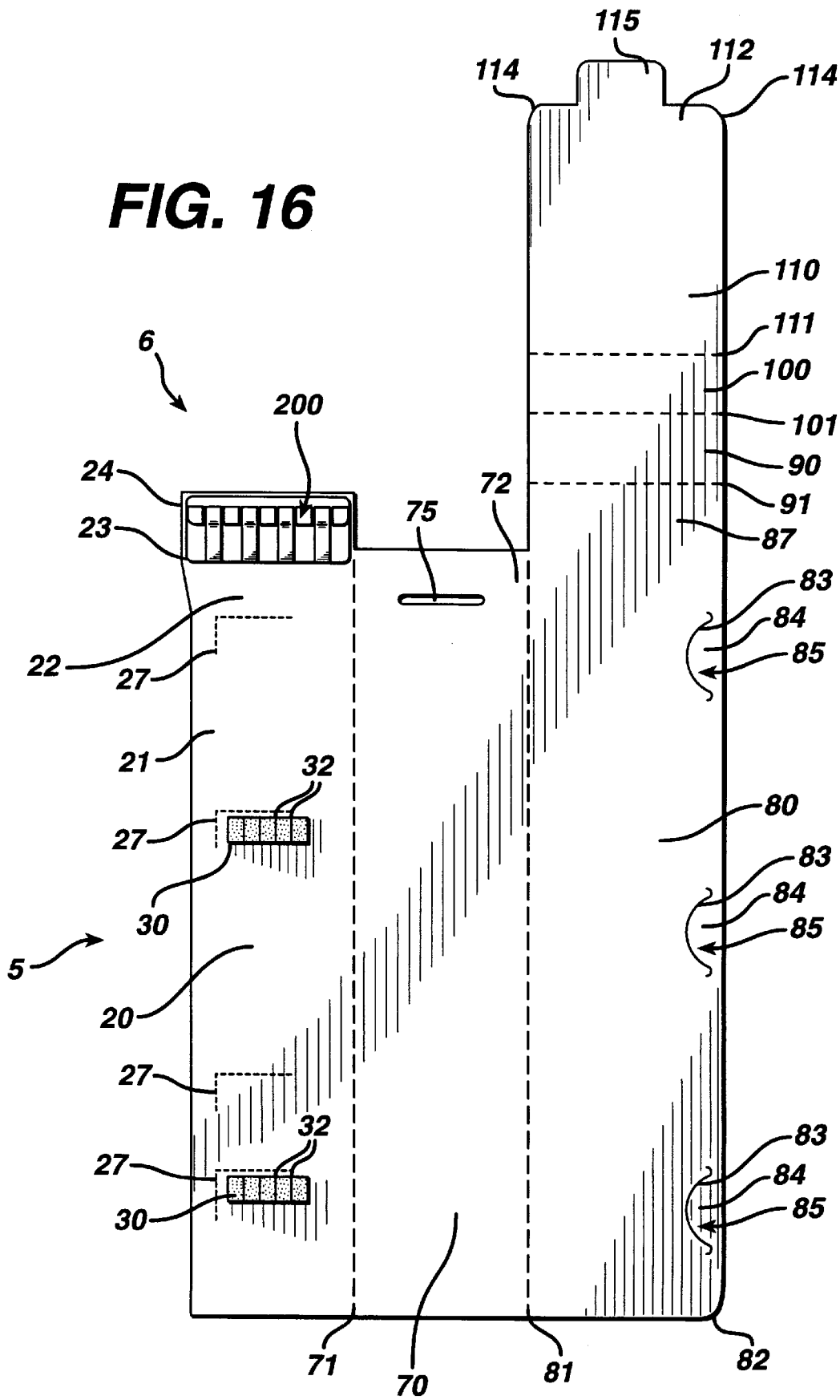
FIG. 16 is a plan view of an alternate embodiment of a package of the present invention having a molded ramped needle park member mounted to the base panel.

An alternate embodiment of the package 5 of the present invention is seen in FIG. 16. The package 6 is identical except that a molded ramp structure 200 as seen in FIG. 15 is placed on the top 24 of base panel 20 in top section 23, and connecting panel 50 and ramp panel 60 are eliminated; and, the park member 40 is also eliminated.

Referring now to FIG. 15, a preferred embodiment of a ramp structure is illustrated. Ramp structure 200 is seen to have a base 210 having a top 211 and a bottom 212. A plurality of projections 220 are seen to extend up from base member 210. The projections 220 are separated by suture retaining slots 250. The projections 220 are seen to have tops 222, distal sides 224, proximal sides 226 and opposed end sides 228. The slots 250 are bordered by sides 228 and base member top 211. The slots 250 have distal open ends 252, proximal open ends 254 and tops 256. Extending upward from base member 210 are the ramp members 260. Ramp members 260 are seen to have top ramped surface 262 having proximal end 264 and distal end 266. The ramp member 260 also is seen to have opposed side members 268. The distal ends of ramp members 260 are seen to intersect the proximal sides 226 of projections 220. The proximal end of ramp 260 is seen to intersect base member 210. The ramp members 260 are in alignment with the projections 220 and spaced so that every other projection 220 has an intersecting ramp member 260 proximal to it. The ramp members 260 are preferably substantially the same width as projections 220. As seen in FIG. 15, double-armed sutures 150 having needles 160 mounted thereto are contained in slots 250. When sutures 150 are withdrawn from package 6, loop 155 slides onto and over ramp member 260.

Figure 12:
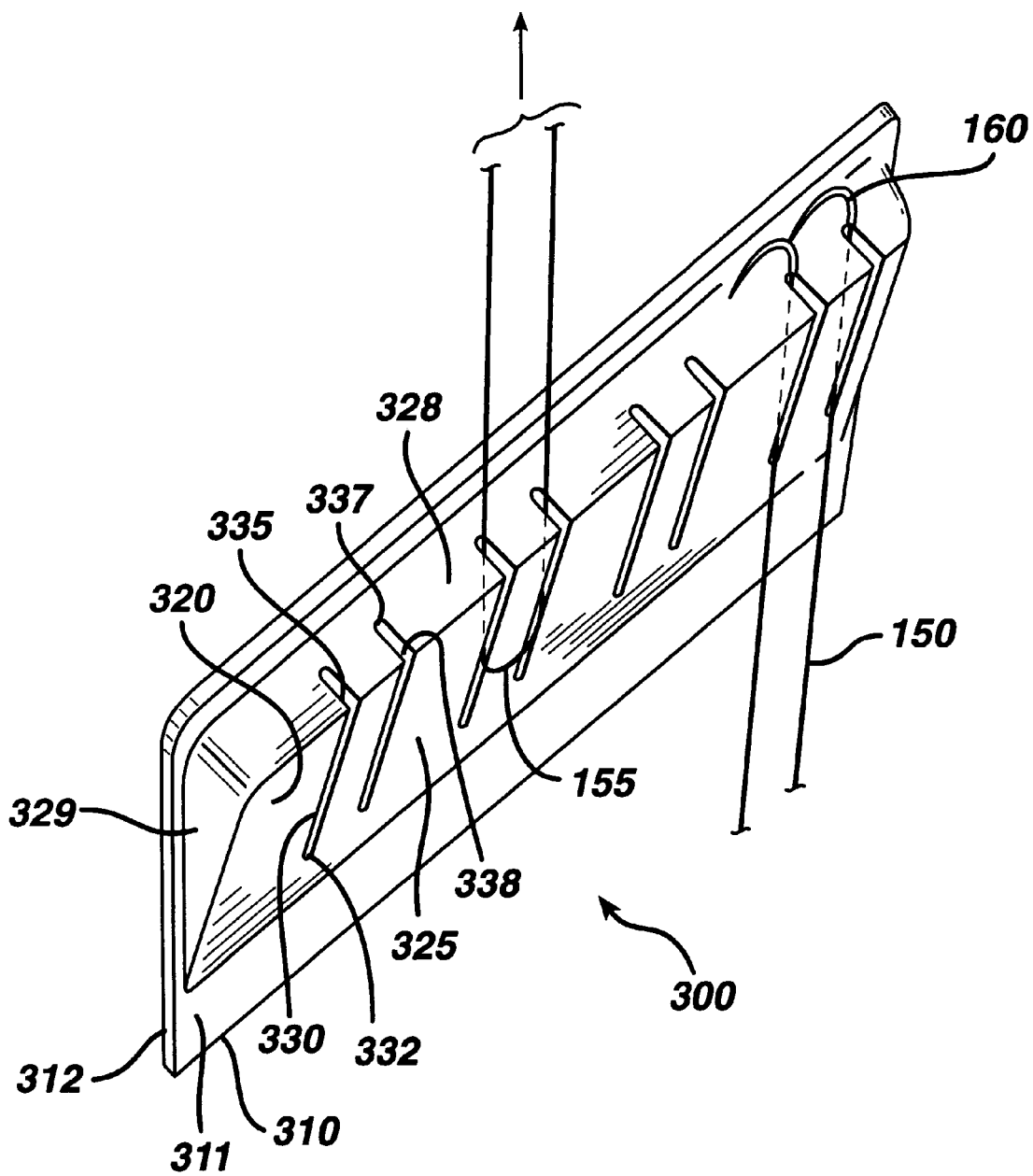
FIG. 12 is a perspective view of a molded ramped needle park useful in the packages of the present invention.

FIG. 12 illustrates another embodiment of a ramp structure 300 of the present invention. The ramp structure is seen to have a base member 310 having top 311 and bottom 312. Extending upward from the top of base member 310 is the ramp member 320. Ramp member 320 is seen to have top ramp surface 325, distal end surface 328 and opposed sides 329. Located in the ramp member 310 are a plurality of slots having top 330, proximal end 332 and distal open end 335. Sutures 150 are seen to be contained within slots 330. The slots 330 are also seen to have bottoms 337 and opposed sides 338.

Figure 13:
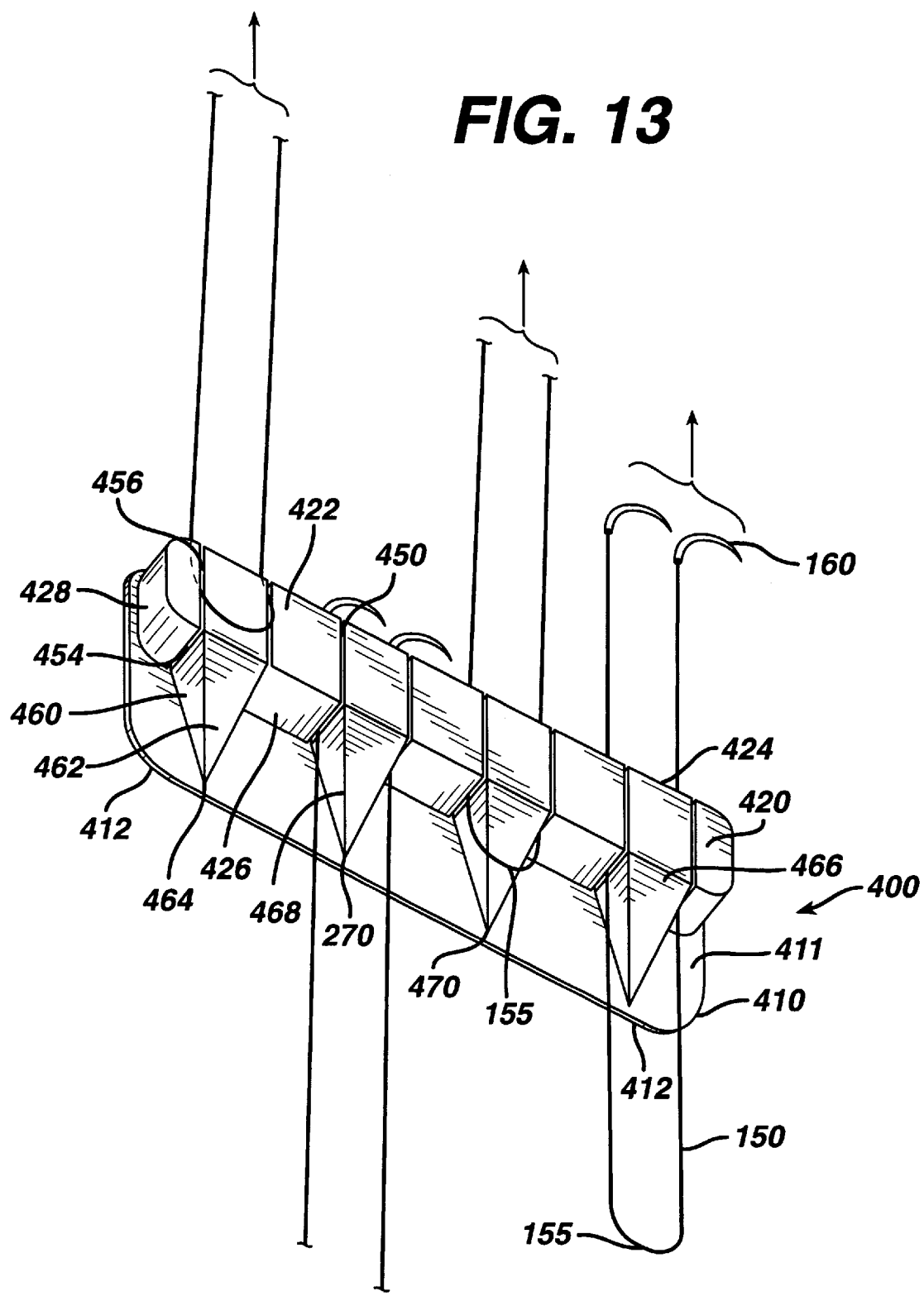
FIG. 13 is a perspective of an alternate embodiment of a molded ramped needle park useful in the packages of the present invention.

Another embodiment of a ramp structure 400 of the present invention is seen in FIG. 13. The ramp structure 400 is seen to have a base member 410 having top 411 and bottom 412. A plurality of projections 420 is seen to extend up from base member 210. The projections 420 are separated by suture retaining slots 450. The projections 420 are seen to have tops 422, distal sides 424, proximal sides 426 and opposed end sides 428. The slots 450 are bordered by sides 428 and base member top 411. The slots 450 have distal open ends 452, proximal open ends 454 and tops 456. Extending upward from base member 410 are the ramp members 460. Ramp members 460 are seen to have top ramp surface 462 having proximal end 464 and distal end 466. The ramp members 460 are also seen to have opposed side members 468. The ramp members 460 are seen to have a pyramidal-like shape and the ramp surface 462 and the side members 468 intersect at a proximal apex 470. Sutures 150 are seen to be contained within slots 450. Suture loop 155 is seen to slide up ramp member 460 when the suture is withdrawn from the package and the park member 400.

Figure 14:
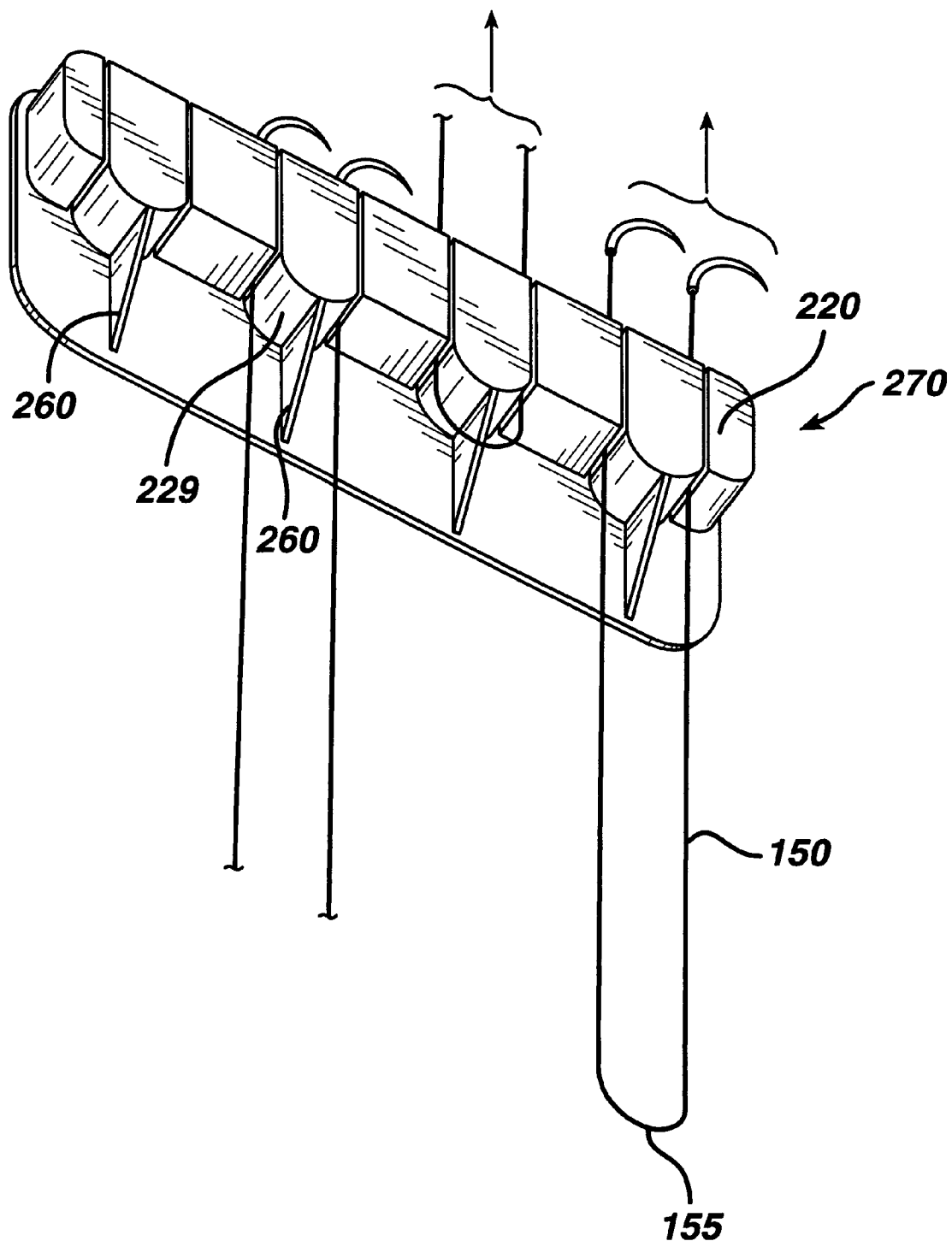
FIG. 14 is a perspective view of yet another embodiment of a molded ramped needle park useful in the package of the present invention.

Yet another embodiment of a ramp structure of the present invention is seen in FIG. 14. The ramp member 270 is seen to be identical to ramp member 220, except that the width of the ramp members 260 is substantially less than the width of the ramp members 260 of ramp structure 200. In addition, the projections 220, which intersect a ramped member 260, are seen to have a curved proximal side 229.

Conventional envelopes useful as outer pouch 10 may be made from polymer films including TYVEK®, polyester copolymers, polypropylene copolymers, combinations thereof, and the like. The envelopes may also be made from polymer film, paper, and foil combinations. The package 5 may also be packaged in a conventional foil packet.

Figure 3:
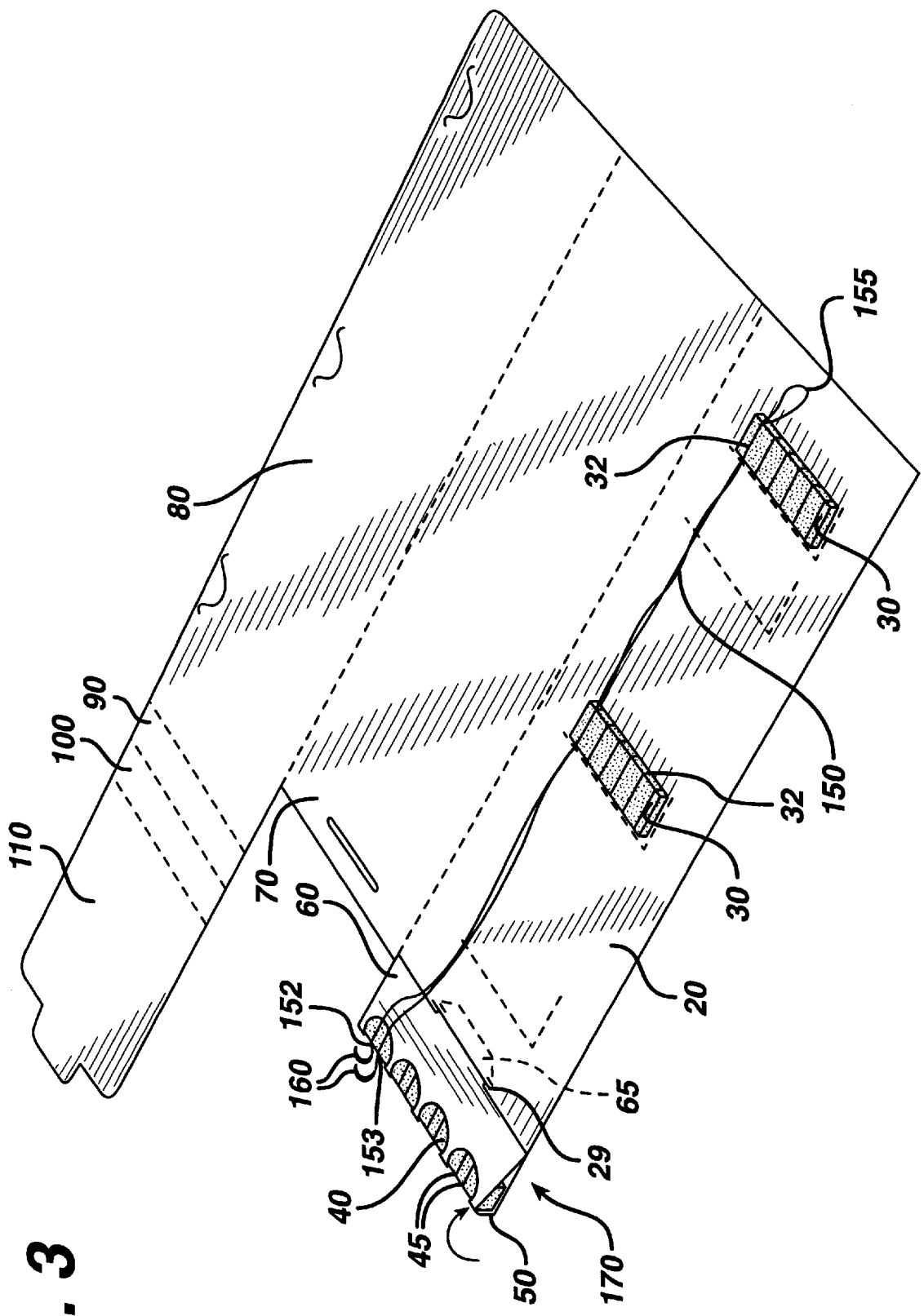
FIG. 3 is a perspective view of a package of the present invention wherein the ramp member has been assembled, and a single, double-armed suture has been mounted in the suture parks and needle parks.
Figure 4:
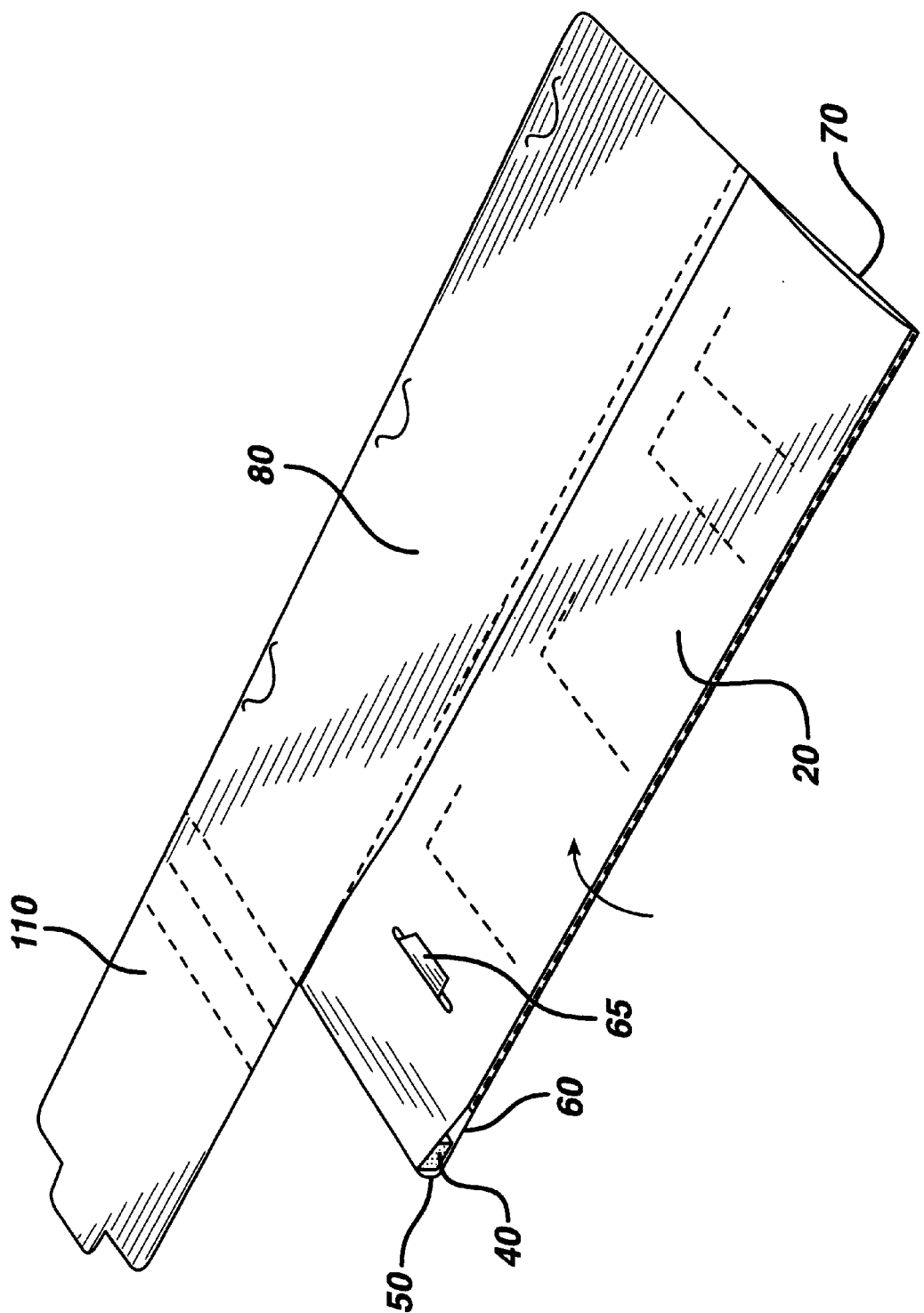
FIG. 4 is a perspective view of a package of the present invention showing the base panel folded over and onto the cover panel.
Figure 5:
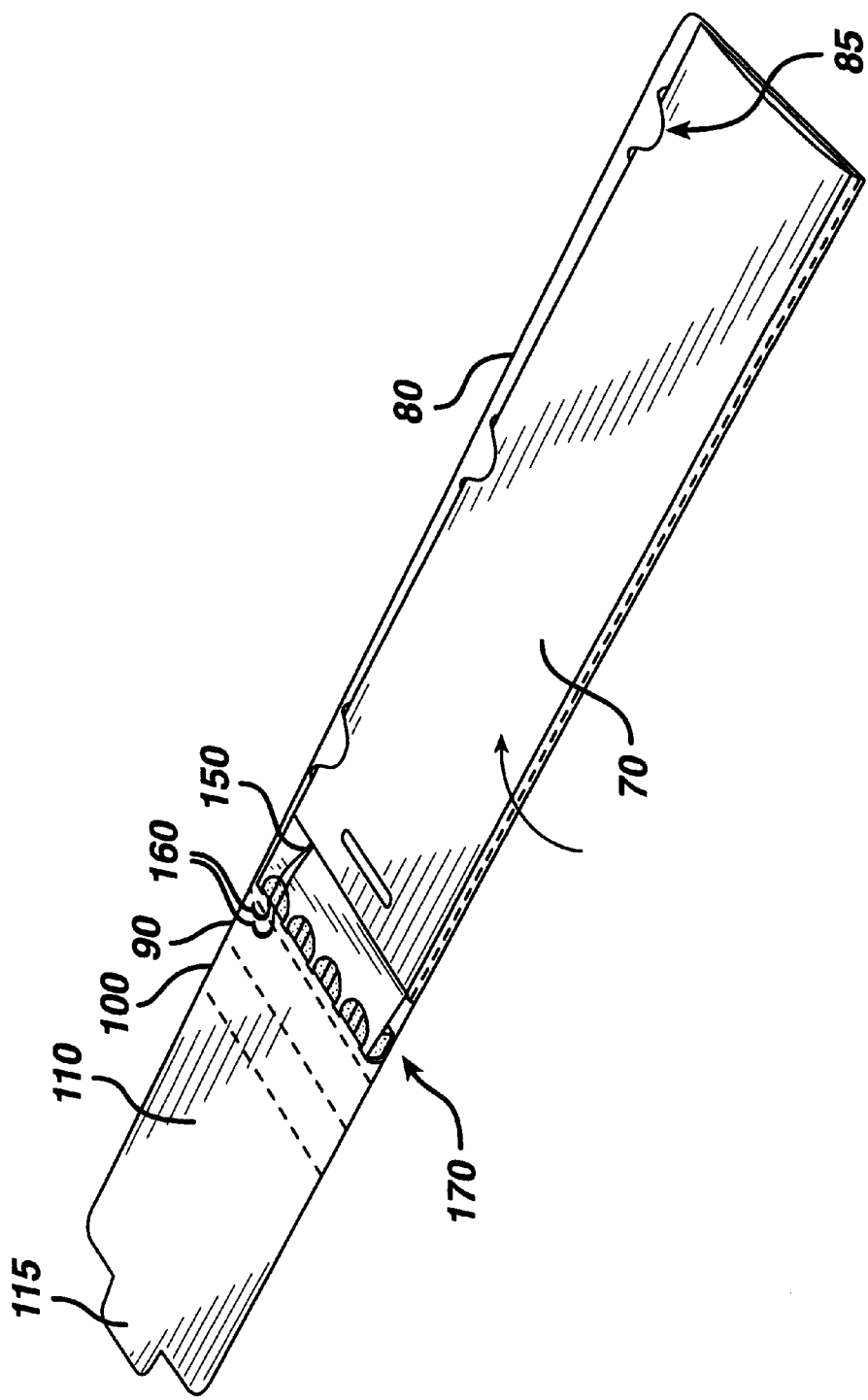
FIG. 5 is a perspective view of a package of the present invention showing the base panel and cover panel folded over onto the closure panel with the edges of the base panel and cover panel locked into tab pockets on the closure panel.
Figure 6:
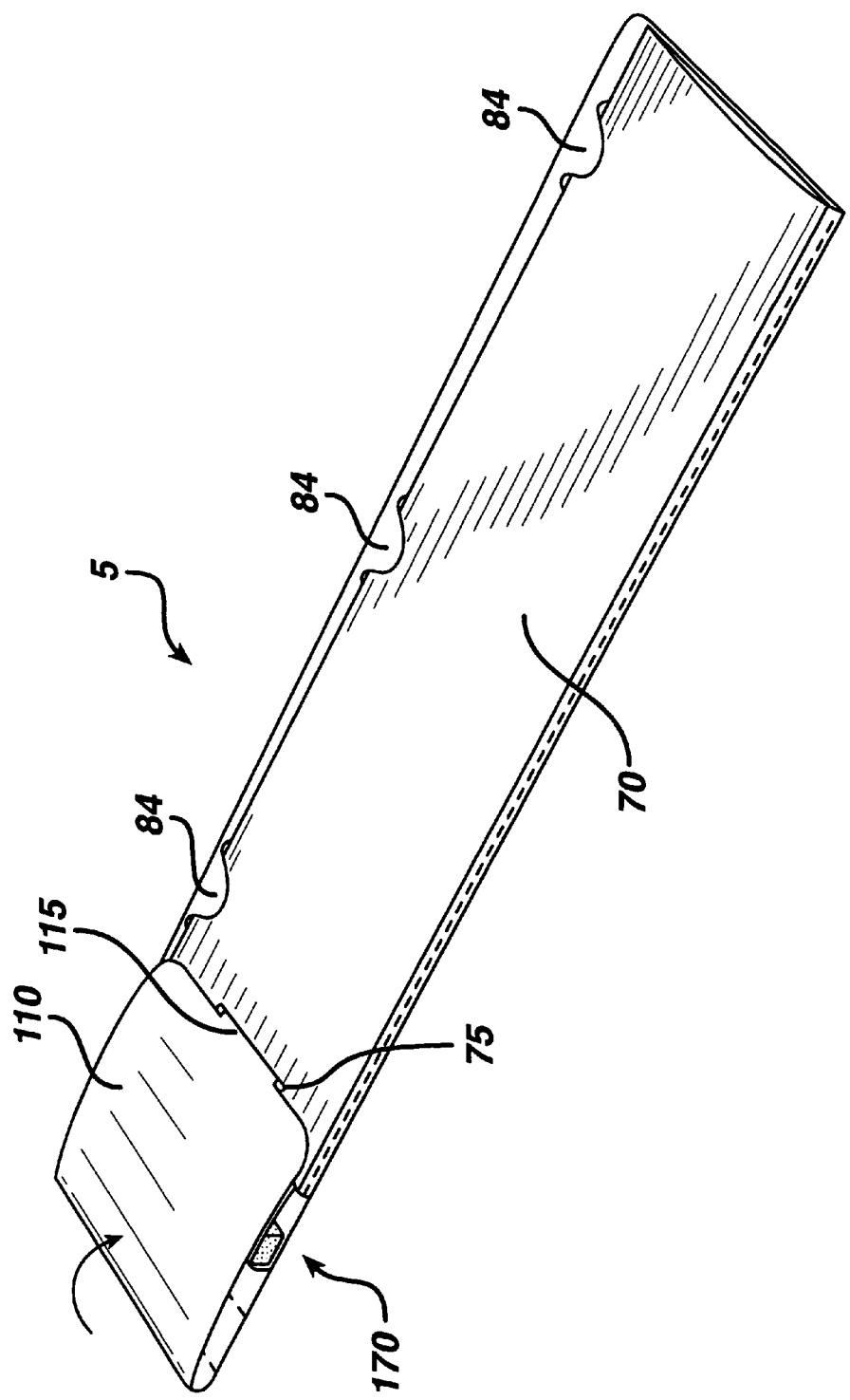
FIG. 6 is a perspective view of a package of the present invention showing the end panel closed over the closure panel with the tab of the end panel engaging a tab pocket in the closure panel.

Referring now to FIGS. 3–6, the assembly of the package 5 is illustrated. As illustrated in FIG. 3, a double-armed suture 150 having ends 152 and 153 and further having needles 160 mounted thereto, is seen to be mounted in the package 5 on the front side of base panel 20. The suture 150 is seen to be folded in half thereby forming loop 155. Prior to mounting the needles 160 and suture 150 on base panel 20, the ramp structure 170 is assembled by rotating panel 50 clockwise about fold line 51 so that panel 50 is perpendicular to base panel 20, and then rotating ramp panel 60 about fold line 61 such that panel 60 is folded on top of the suture park 40 and the tab 65 is inserted into slit 29, thereby forming the ramp structure 170. The openings 55 in the ramp structure 170 are in alignment with pairs of the slits 45 in the suture park 40 to allow the ends 152 and 153 of suture 150 to be placed therein. As seen in FIG. 3, the ends 152 and 153 of the suture 150 are placed in adjacent slits 41 in the suture park 140. The needles 160 and adjacent sections of suture 150 are seen to extend beyond the end of the ramp structure 170. Next, as illustrated in FIG. 4, the base panel 20 is rotated in a clockwise manner about fold line 71 onto the front side of the cover panel 70. Next, the cover panel 70 and the base panel 20 are rotated in a clockwise manner about fold line 81 onto the front side of closure panel 80. In addition, the edges of panels 20 and 70 along fold line 71 are inserted into the tab pockets 85. Next, as seen in FIG. 6, the end panel 110 is rotated in a counter-clockwise manner on top of the back side closure panel 80 such that tab member 115 is inserted into slot 75., thereby closing the package 5 and completing the assembly. Package 5 is then typically inserted into a conventional outer pouch 10 as seen in FIG. 1, which is then sealed. The pouch 10 and the package 5 are typically sterilized in a conventional sterilization cycle. Those skilled in the art will appreciate that the packages 6 of the present invention having molded ramp structures 200, 270, 300 and 400 will be assembled in a similar manner. However, since packages 6 do not have connecting panel 50, ramp panel 60 and park members 40, those steps will not be required in assembly. However, the ramp structures will preferably be mounted to the base panel 20 as described herein prior to assembly of the package 6.

Figure 7:
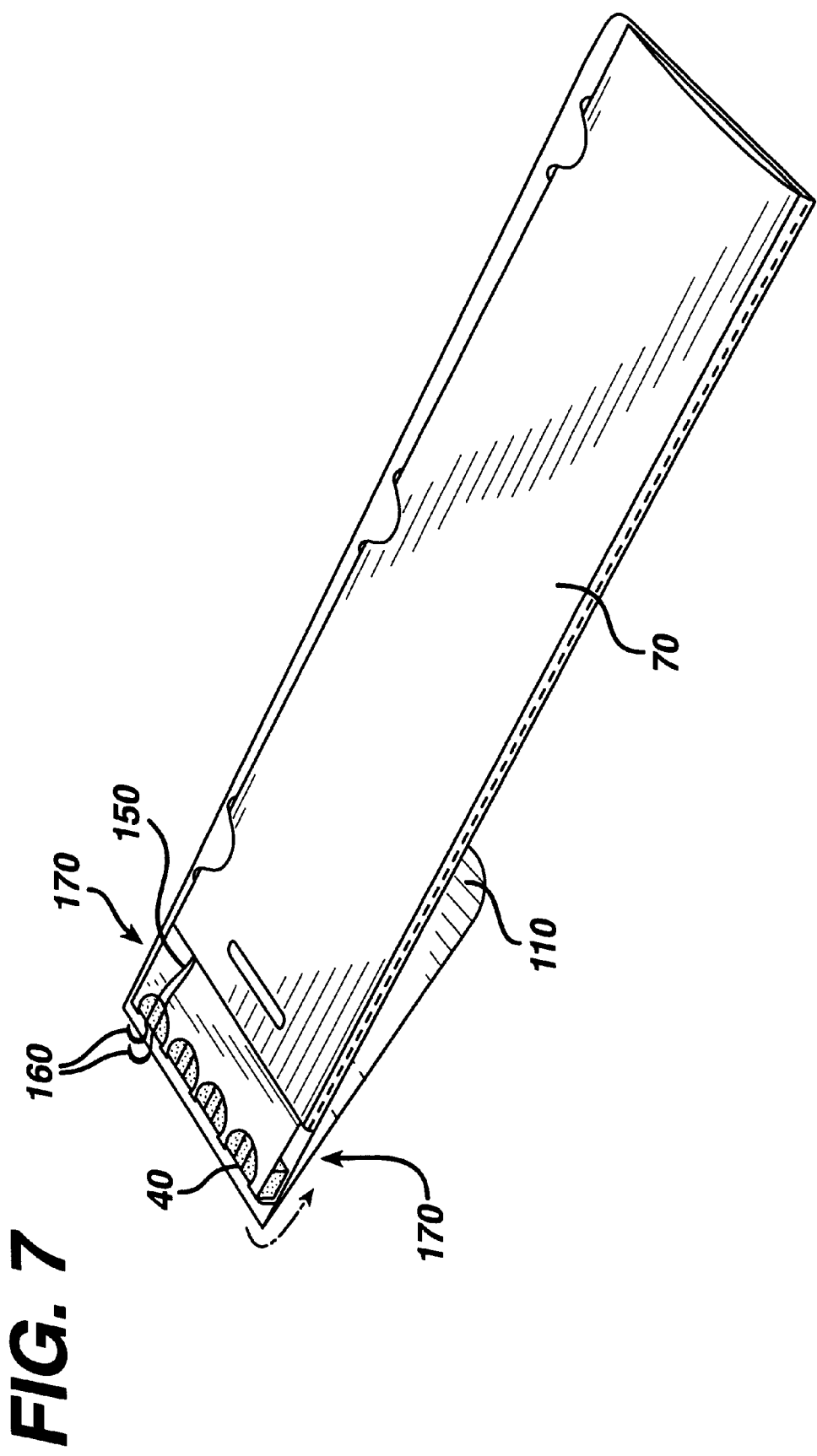
FIG. 7 is a perspective view of a package of the present invention illustrating how the assembled package is opened to remove the double-armed needles and sutures by folding back the end panel and connecting panels in order to expose the needles in the suture park; also illustrated is the suture riding over the ramp adjacent to the suture park.
Figure 8:
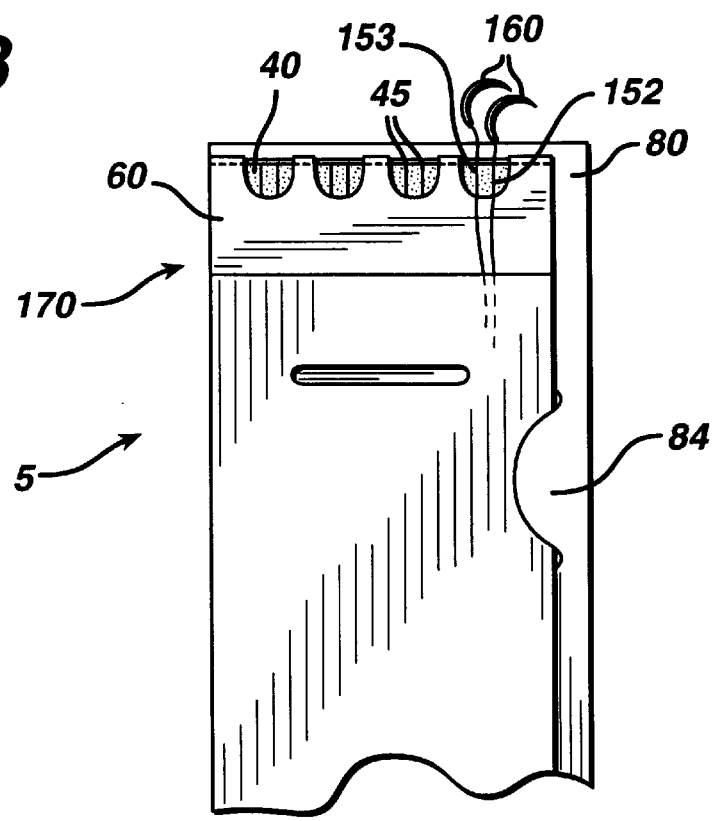
FIG. 8 is a partial enlarged top view of the top end of the package of FIG. 7 illustrating the suture park and ramp member and double armed sutures.
Figure 9:
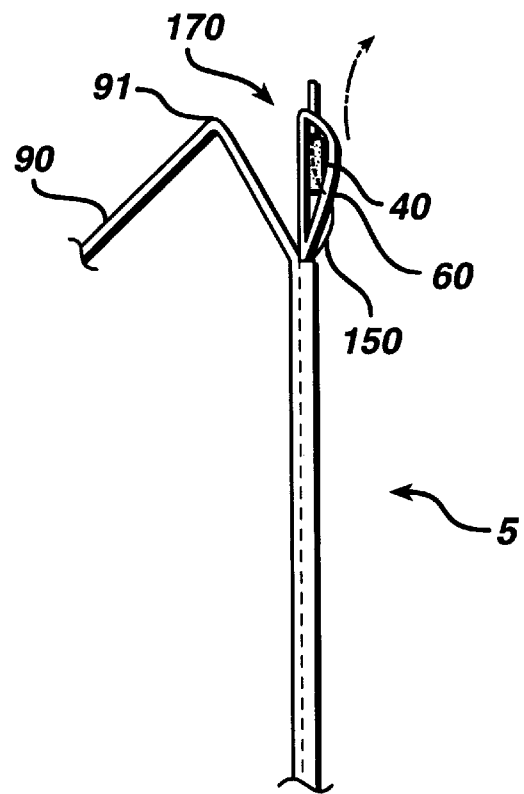
FIG. 9 is a partial side view of the package of FIG. 8.
Figure 10:
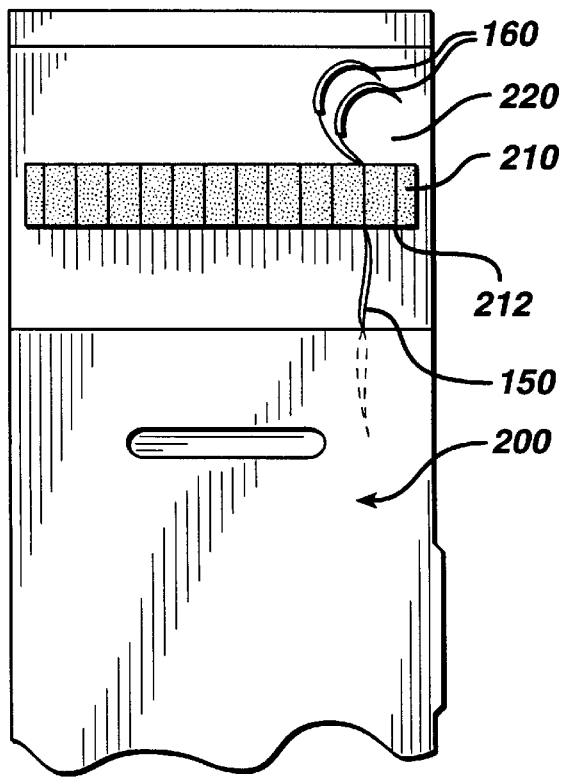
FIG. 10 is a partial top view of a package of prior art illustrating an opened end of the package wherein the needles and sutures are parked in a foamed needle park.

In order to remove double-armed sutures 150 and needles 160 from the package 5 of the present invention, the first step is for the operating room professional to remove the package 5 from the pouch 10 by peeling the pouch 10 apart. Then, as seen in FIG. 7 and FIG. 8, the end panel 110 is rotated in a counter-clockwise manner about fold line 101 thereby exposing the needles 160 and the ends of the suture 150. The operating room professional then grasps a first needle 160 adjacent to end 152 with a conventional needle grasper and proceeds to pull the entire suture 150 and the other needle 160 out from the package. As the suture 150 is pulled out from the package it slides over the ramped structure 170 until end 153 exits the park 40, thereby preventing the suture from engaging any of the slits 45 in the needle/suture park 40. A right and left handed arming feature of the packages of the present invention is seen in FIG. 9. By rotating the end panel 110 along with the first and second connecting panels 100 and 90 about the fold line 91, the needles may be armed from the back side of the package 5. This facilitates suturing by a left handed person. The top end of closure panel 80 is seen in FIG. 9 to be hyper-rotated merely for purpose of illustration. The removal of double-armed sutures from packages 6 will be done in a similar manner.

Figure 11:
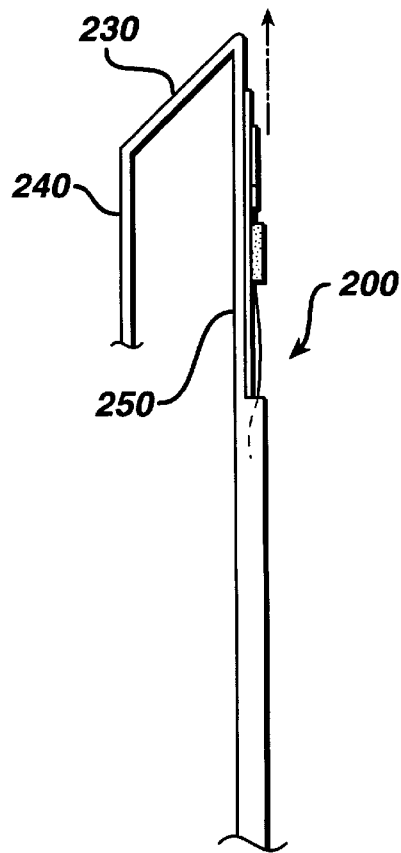
FIG. 11 is a partial side view of the package of FIG. 10.

A folder package of the prior art for double-armed suture packages is seen in FIGS. 12 and 11. The package 200 is seen to have a needle park 210, a base panel 220, a connecting panel 230, an end panel 240 and a closure panel 250. The park 210 is seen to have slits 212. It can be appreciated that the health care professional when removing the double-armed suture from the needle suture park 210 may inadvertently cause the suture to become entrapped between two adjacent slits so that it cannot be removed from the suture park. This problem is eliminated by using the ramp structure 170 of the present invention which would allow the suture to slip over the top of the ramp structure 170 thereby preventing it from re-engaging a slit 212 in the park 210 and becoming hung-up. This also allows separation of needles. It also indicates to the health care professional that a pair of needles belongs together.

It will be appreciated by those skilled in the art that the size of the packages 5 and 6 and the panels will vary in accordance with the size of the sutures and needles. The packages 5 and 6 and their panels will be of sufficient size to effectively contain a particular suture and needle assembly as illustrated and described herein.

The packages 5 and 6 of the present invention containing sutures and needles are typically further packaged by insertion into a conventional polymeric envelope 10 or a conventional foil packet, which is then sealed. As previously mentioned, a conventional polymeric envelope typically is made from conventional materials such as TYVEK®, paper polyfoil, polyester copolymer, polypropylene copolymer, combinations thereof, and the like.

The packaged medical devices are typically sterilized using conventional sterilization equipment and processes. Examples of the sterilization processes which can be used on the package needles and sutures packaged in the foldable packages 5 and 6 of the present invention include conventional sterilization processes such as Co 60, irradiation, ethylene oxide, methylene bromide, and the like.

The ramp structures 170, 200, 270 and 400 of the present invention may be constructed of injection molded or thermoformed pieces and the like and equivalents thereof, if so desired, in addition to the panel structures shown and described herein. In addition, the ramp structure 170 may be made from shaped foam. Or the ramp structure 170 may be made from foldable panels that are not foldably attached to package 5. Such structures would be mounted to base panel 20 using conventional mounting methods including mechanical fasteners and glues. It is preferred to use the ramp structures 170, 200, 270, 300 and 400 of the present invention in conjunction with needle parks in packages for double-armed sutures. However, the ramp structures can also be used in single-armed suture packages and will similarly prevent suture from becoming engaged or re-engaged with a needle park.

The folder packages 5 and 6 of the present invention are preferably constructed from any material having the required structural characteristics such that the material can be readily die cut, and scored. In addition, the material must be easily folded and sterilizable. The materials include those known in the art for packaging sutures and medical devices, including paper, plastic, foils, and laminates of one or more thereof. However, it is particularly preferred in the practice of the present invention to utilize a heavyweight, relatively stiff, medical grade paper or paperboard such as 0.007–0.016" suture board.

The advantages of the packages of the present art are numerous. The packages 5 and 6 of the present invention have many advantages. It is easy to manufacture out of conventional materials. The package 5 is extremely easy to assemble. Other advantages include the ability to separate needles in different slits in a needle park. The needles and sutures can be easily armed without catching on the needle/suture park. The package provides for right and left hand arming of needle holders. The packages are economical. And, the packages provide for identification of needle pairs by the cutouts in the ramp structure.

Although this invention has been shown and described with respect to detailed embodiments thereof, it will be understood by those skilled in the art that various changes of form and detail thereof may be made without departing from the spirit and scope of the present invention.

We claim:

1. A foldable package for a surgical suture, the package comprising:

a base panel, said base panel having opposed first and second major sides and opposed top and bottom minor sides, said panel having a top and a bottom;

a cover panel having first and second major sides and opposed first and second minor sides, wherein the second major side of the base panel is foldably connected to the first minor side of the cover panel;

a closure panel comprising first and second opposed major sides and first and second opposed minor sides, wherein the first major side of the closure panel is foldably connected to the second major side of the cover panel;

an end panel foldably connected to the first minor side of the closure panel;

means for locking the closure panel to the base panel and cover panel;

means for locking the end panel to the cover panel; and, a molded suture retaining ramp structure mounted to the base panel adjacent to the top minor side.

2. The package of claim 1 wherein the means for locking the closure panel to the base panel and cover panel comprises at least one tab pocket.

3. The package of claim 1 wherein the means for locking the end panel to the cover panel comprises a tab extending from the end panel, and a tab pocket in the cover panel for receiving the tab.

4. A foldable package for a surgical suture, the package comprising:

a base panel, said base panel having opposed first and second major sides and opposed top and bottom minor sides, said panel having a top and a bottom;

a cover panel having first and second major sides and opposed first and second minor sides, wherein the second major side of the base panel is foldably connected to the first minor side of the cover panel;

a closure panel comprising first and second opposed major sides and first and second opposed minor sides, wherein the first major side of the closure panel is foldably connected to the second major side of the cover panel;

an end panel foldably connected to the first minor side of the closure panel;

means for locking the closure panel to the base panel and cover panel;

means for locking the end panel to the cover panel; and, a molded suture retaining ramp structure mounted to the base panel adjacent to the top minor side, wherein the means for locking the closure panel to the base panel and cover panel comprises at least one tab pocket, wherein the means for locking the end panel to the cover panel comprises a tab extending from the end panel, and a tab pocket in the cover panel for receiving the tab; and, wherein the suture retaining ramp structure comprises:
  a base member having a top side and a bottom side;
  a plurality of projections extending up from the top side of the base member, said projections having a top side, a proximal side, a distal side and opposed end sides, said projections separated from each other by slots; and,
  a plurality of ramped members extending up from the top side of the base member, the ramped members having a sloped top side, a pair of opposed sides, a distal end and a proximal end, wherein the distal side of each ramped member intersects the proximal side of a projection, and wherein the proximal end of each ramped member intersects the top side of a base member, and wherein the distal end of each sloped top side intersects a top side of a projection.

5. The package of claim 1, additionally comprising at least one connecting panel foldably connected between the closure panel and the end panel.

6. The package of claim 1, wherein the surgical suture is a double-armed suture.

7. A suture retaining ramp comprising:

a base member having a top side and a bottom side;

a plurality of projections extending up from the top side of the base member, said projections having a top side, a proximal side, a distal side and opposed end sides, said projections separated from each other by slots; and, a plurality of ramped members extending up from the top side of the base member, the ramped members having a sloped top side, a pair of opposed sides, a distal end and a proximal end, wherein the distal side of each ramped member intersects the proximal side of a projection, and wherein the proximal end of each ramped member intersects the top side of a base member, and wherein the distal end of the sloped top side of each ramped member intersects the top side of a projection.

* * * * *

UNITED STATES PATENT AND TRADEMARK OFFICE
CERTIFICATE OF CORRECTION

PATENT NO. : 6,015,042
DATED : January 18, 2000
INVENTOR(S) : Robert James Cerwin, Deborah M. Transue, Marvin Alpern It is certified that error appears in the above-identified patent and that said Letters Patent is hereby corrected as shown below:

Title page, under
Attorney, Agent, or Firm: Emmil should be "Emil"

Signed and Sealed this

Fifth Day of December, 2000

*Attest:*

Q. TODD DICKINSON

*Attesting Officer*     *Director of Patents and Trademarks*